(12) United States Patent
Tolar et al.

(10) Patent No.: US 10,471,029 B2
(45) Date of Patent: Nov. 12, 2019

(54) METHODS FOR TREATING NEUROLOGICAL DISORDERS

(71) Applicant: Alzheon, Inc., Framingham, MA (US)

(72) Inventors: Martin Tolar, Framingham, MA (US); John A. Hey, Lexington, MA (US); Petr Kocis, Framingham, MA (US); Jeremy Yu, Framingham, MA (US)

(73) Assignee: Alzheon, Inc., Framingham, MA (US)

( * ) Notice: Subject to any disclaimer, the term of this patent is extended or adjusted under 35 U.S.C. 154(b) by 0 days.

(21) Appl. No.: 15/127,565

(22) PCT Filed: Mar. 23, 2015

(86) PCT No.: PCT/US2015/022058
§ 371 (c)(1),
(2) Date: Sep. 20, 2016

(87) PCT Pub. No.: WO2015/143447
PCT Pub. Date: Sep. 24, 2015

(65) Prior Publication Data
US 2017/0172952 A1   Jun. 22, 2017

Related U.S. Application Data

(60) Provisional application No. 61/968,595, filed on Mar. 21, 2014.

(51) Int. Cl.
| | |
|---|---|
| A61K 31/185 | (2006.01) |
| A61K 38/05 | (2006.01) |
| G01N 33/68 | (2006.01) |
| C12Q 1/6883 | (2018.01) |
| A61K 47/54 | (2017.01) |
| G16H 10/20 | (2018.01) |
| G06F 19/00 | (2018.01) |

(52) U.S. Cl.
CPC .......... *A61K 31/185* (2013.01); *C12Q 1/6883* (2013.01); *C12Q 2600/106* (2013.01); *C12Q 2600/158* (2013.01); *G06F 19/325* (2013.01); *G16H 10/20* (2018.01)

(58) Field of Classification Search
None
See application file for complete search history.

(56) References Cited

U.S. PATENT DOCUMENTS

| | | |
|---|---|---|
| 5,698,155 A | 12/1997 | Grosswald et al. |
| 8,748,656 B2 | 6/2014 | Kong et al. |
| 9,499,480 B2 | 11/2016 | Kong et al. |
| 10,238,611 B2 | 3/2019 | Kong et al. |
| 2005/0031651 A1 | 2/2005 | Gervais et al. |
| 2006/0079578 A1 | 4/2006 | Laurin et al. |
| 2008/0146642 A1 | 6/2008 | Kong et al. |
| 2009/0182056 A1 | 7/2009 | Laurin et al. |
| 2010/0113591 A1 | 5/2010 | Kong et al. |
| 2010/0183513 A1 | 7/2010 | Froestl et al. |
| 2012/0071468 A1 | 3/2012 | John et al. |
| 2014/0220122 A1 | 8/2014 | Kong et al. |
| 2014/0328856 A1 | 11/2014 | Gelmont et al. |
| 2017/0095430 A1 | 4/2017 | Kong et al. |
| 2018/0250249 A1 | 9/2018 | Abushakra et al. |

FOREIGN PATENT DOCUMENTS

| | | |
|---|---|---|
| CN | 101578269 A | 11/2009 |
| CN | 101600730 A | 12/2009 |
| JP | 2007-502418 | 2/2007 |
| JP | 2010-514674 | 5/2010 |
| WO | WO 94/09155 A1 | 4/1994 |
| WO | WO-2005/060393 A2 | 7/2005 |
| WO | WO-2009/019534 A2 | 2/2009 |
| WO | WO 2012/006329 A2 | 1/2012 |
| WO | WO-2017/044840 A1 | 3/2017 |

OTHER PUBLICATIONS

ClinicalTrials.gov (NTC00574131) Dec. 10, 2007.*
Caltagirone C. et al., "The potential protective effect of tramiprosate (homotaurine) against Alzheimer's disease: a review," Aging Clinical and Experimental Research, 2012, vol. 24, No. 6, pp. 580-587.
Wright, T. M., "Tramiprosate", Drugs of Today, 2006, vol. 42, No. 5, pp. 291-298.
Abushakra, S. et al. Clinical Benefits of Tramiprosate in Alzheimer's Disease Are Associated with Higher No. of APOE4 Alleles: The "APOE4 Gene-Dose Effect", J Prey Alzheimers Dis. 2016;3(4):219-228.
Abushakra, S. et al. "Tramiprosate, an oral amyloid anti-aggregation agent, shows robust cognitive efficacy in APOE4/4 homozygous AD patients: efficacy and safety analyses from two Phase 3 trials", Neurobiology of Aging 2016;39:S22.
Aisen, P.S. et al. "Tramiprosate in mild-to-moderate Alzheimer's disease—a randomized, double-blind, placebo-controlled, multi-centre study (the Alphase Study)", Arch Med Sci. Feb. 2011;7(1):102-11.
Munzar, M. et al. "Clinical study of a urinary competitive ELISA for neural thread protein in Alzheimer disease", Neurol Clin Neurophysiol. 2002; 2002(1): 2-8.
Sleegers et al., "The pursuit of susceptibility genes for Alzheimer's disease: progress and prospects", Trends in Genetics, vol. 26, No. 2, Feb. 2010, pp. 84-93.

* cited by examiner

Primary Examiner — James H Alstrum-Acevedo
Assistant Examiner — Tara L Martinez
(74) Attorney, Agent, or Firm — Cooley LLP; Michael Tuscan; Thomas J. Paxton (57) ABSTRACT

Disclosed herein are methods and compositions for treating, ameliorating, and/or preventing Alzheimer's disease in ApoE4-postitive patients using particular compounds and compositions thereof.

14 Claims, 7 Drawing Sheets

Figure 1: Tramiprosate Treatment of AD Patients Improves ADAS-Cog Score:

Figure 4: Improved brain accumulation of Tramiprosate administered as Val-APS vs tramiprosate Figure 5: Extended t1/2 of Tramiprosate administered as Val-APS Figure 6: Reduced Formation of Metabolite NRM5074 Following Val-APS administration Figure 7: Summary of Improved PK with loose-filled Val-APS capsule vs Tramiprosate loose-filled capsule and tablet

| Parameters | Val-APS LF Capsule (N=12) | Tramiprosate LF Capsule (N=12) | Tramiprosate MR Tablet (N=12) |
|---|---|---|---|
| Cmax (ng/ml) | 628 ± 100 | 769 ± 228 | 506 ± 187 |
| Tmax (h) | 2.0 | 1.0 | 4.5 |
| $AUC_{0-t}$ (h x ng/mL) | 2,680 ± 448 | 3,268 ± 1,128 | 2,355 ± 747 |
| $T_{1/2}$ (h) | 14.9 ± 3.9 | 5.9 ± 5.2 | 4.9 ± 2.6 |

Figure 8: Effect of 3APS on Cognition in ApoE4 sub-populations

METHODS FOR TREATING NEUROLOGICAL DISORDERS

CROSS-REFERENCE TO RELATED APPLICATIONS

This application is a U.S. National Phase application, filed under 35 U.S.C. § 371(c), of International Application No. PCT/US2015/022058, filed Mar. 23, 2015, which claims the benefit of and priority to U.S. provisional patent application No. U.S. 61/968,595, filed Mar. 21, 2014, each of which are incorporated herein by reference in their entireties for all purposes.

This application incorporates by reference for all purposes the contents of: U.S. Application Publication Nos. 2008/0146642, filed Oct. 12, 2007, 2009/0182056, filed Jan. 30, 2009, and 2010/0113591 filed Nov. 5, 2009.

BACKGROUND OF THE INVENTION

Alzheimer's disease (AD) is a progressive degenerative disease of the brain primarily associated with aging. Prevalence of AD in the United States in 2000 was close to 4.5 Million. It was estimated that about one in ten individuals over 65 and nearly half of those over 85 are affected by Alzheimer's disease. Approximately 360,000 patients will be diagnosed with AD each year in the United States alone.

Clinical presentation of AD is characterized by loss of memory, cognition, reasoning, judgment, and orientation. As the disease progresses, motor, sensory, and linguistic abilities are also affected until there is global impairment of multiple cognitive functions. These cognitive losses occur gradually, but typically lead to severe impairment and eventual death in the range of four to twelve years.

Alzheimer's disease is characterized by two major pathologic observations in the brain: neurofibrillary tangles and beta amyloid (or neuritic) plaques, comprised predominantly of an aggregate of a peptide fragment know as beta amyloid peptide Aβ. Individuals with AD exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders.

SUMMARY OF THE INVENTION

The present disclosure is generally related to treatment of neurological disorders, particularly Alzheimer's disease in specific sub-populations that have one or more copies of the ApoE4 (or ε4) allele.

L-Valyl-3-aminopropanesulfonate (Val-APS) is an orally available small molecule prodrug of tramiprosate with improved pharmaceutical properties. Tramiprosate was advanced to a ~2,000 patient Phase 3 program which completed in 2007. However, the Val-APS prodrug demonstrates key advantages over tramiprosate including improved GI tolerability, reduced nausea & vomiting, and decreased inter-subject PK variability. In addition, administering the prodrug provides for once-daily dosing due to an advantageously extended $t_{1/2}$ of 14.9 hours. Notably, oral administration of Val-APS provides a ~2-fold increase in plasma and brain exposure of tramiprosate in animals compared to tramiprosate administered at equimolar doses. Thus the present disclosure provides for administration of certain compounds including val-APS to ApoE4-positive patients for the treatment of Alzheimer's Disease.

Val-APS:

BRIEF DESCRIPTION OF FIGURES

FIG. 8 illustrates the advantageous effects of tramiprosate, the active agent of Val-APS, in certain sub-populations segregated based on Apo E4 status. The data established substantially improved ADAs-cog scores vs placebo over time. Data is presented at 13 weeks, 26 weeks, 39 weeks, 52 weeks, 65 weeks, and 78 weeks. The first column shows patients homozygous for ApoE4 ("ApoE4+/+"), the second column shows combined data from ApoE4 heterozygous and homozygous patients "ApoE4 all-comers", the third column shows patients negative for ApoE4 (Non-ApoE4). ApoE4 prevalence correlates with improved cognition scores.

DETAILED DESCRIPTION OF THE INVENTION

Definitions

The following definitions are used in connection with the disclosure: The term "subject," as used herein unless otherwise defined, is a mammal, e.g., a human, mouse, rat, guinea pig, dog, cat, horse, cow, pig, or non-human primate, such as a monkey, chimpanzee, or baboon. In one embodiment, the subject is a human.

The term "pharmaceutically acceptable salt," as used herein unless otherwise defined, is a salt of a basic group, such as an amino group, or of an acidic group, such as a carboxyl group, on the compounds disclosed herein. Illustrative salts of a basic group include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, and pamoate (i.e., 1,1'-methylene-bis-(2-hydroxy-3-naphthoate)) salts. Illustrative salts of an acidic group include, but are not limited, to lithium, sodium, potassium, calcium, magnesium, aluminum, chromium, iron, copper, zinc, cadmium, ammonium, guanidinium, pyridinium, and organic ammonium salts.

The terms "hydrate" and "solvate" as used herein and unless otherwise defined, describe a compound or salts thereof, which further include a stoichiometric or non-stoichiometric amount of water or other solvent bound by non-covalent intermolecular forces.

An "effective amount" when used in connection with another therapeutic agent is an amount that is effective for treating or preventing a Condition in combination with a compound. "In combination with" includes administration within the same composition and via separate compositions; in the latter instance, the other therapeutic agent is effective for treating or preventing a Condition during a time when the compound exerts its prophylactic or therapeutic effect, or vice versa.

The term "about" when used in connection with a referenced numeric indication means the referenced numeric indication plus or minus up to 10% of that referenced numeric indication. For example, the language "about 50" covers the range of 45 to 55.

The term "amino acid" generally refers to an organic compound comprising both a carboxylic acid group and an amine group. The term "amino acid" includes both "natural" and "unnatural" or "non-natural" amino acids. Additionally, the term amino acid includes O-alkylated or N-alkylated amino acids, or S-alkylated or S-substituted or P-containing amino acids, as well as amino acids having nitrogen or oxygen or sulfur or phosphor-containing side chains (such as Lys, Orn, or Ser, Met) in which the nitrogen or oxygen or sulfur or phosphor atom has been acylated or alkylated. In some aspects, the nitrogen, oxygen, sulfur, phosphor atom of the side chains is derivatized with other than acyl or alkyl groups Amino acids may be pure L or D isomers or mixtures of L and D isomers, including racemic mixtures.

The term "natural amino acid" and equivalent expressions refer to L-amino acids commonly found in naturally occurring proteins. Examples of natural amino acids include, without limitation, alanine (Ala), cystein (Cys), aspartic acid (Asp), glutamic acid (Glu), phenylalanine (Phe), glycine (Gly), histidine (His), isoleucine (Ile), lysine (Lys), leucine (Leu), methionine (Met), asparagine (Asp), proline (Pro), glutamine (Gln), arginine (Arg), serine (Ser), threonine (Thr), valine (Val), tryptophan (Trp), tyrosine (Tyr), β-alanine (β-ALA), In other aspects the amino acid may not be an L-amino acid. For example, γaminobutyric acid (GABA).

The term "unnatural amino acid" refers to any derivative of a natural amino acid including D forms, and α and β-amino acid derivatives and any synthetic compound containing amino and carboxyl groups The terms "unnatural amino acid" and "non-natural amino acid" are used interchangeably herein and are meant to include the same moieties. It is noted that certain amino acids, e.g., hydroxyproline, that are classified as a non-natural amino acid herein, may be found in nature within a certain organism or a particular protein. Amino acids with many different protecting groups appropriate for immediate use in the solid phase synthesis of peptides are commercially available. In addition to the twenty most common naturally occurring amino acids, the following examples of non-natural amino acids and amino acid derivatives may be used according (common abbreviations in parentheses): 2-aminoadipic acid (Aad), 3-aminoadipic acid (β-Aad), 2-aminobutyric acid (2-Abu), α,β-dehydro-2-aminobutyric acid (8-AU), 1-aminocyclopropane-1-carboxylic acid (ACPC), aminoisobutyric acid (Aib), 3-aminoisobutyric acid (β-Aib), 2-amino-thiazoline-4-carboxylic acid, 5-aminovaleric acid (5-Ava), 6-aminohexanoic acid (6-Ahx), 2-aminoheptanoic acid (Ahe), 8-aminooctanoic acid (8-Aoc), 11-aminoundecanoic acid (11-Aun), 12-aminododecanoic acid (12-Ado), 2-aminobenzoic acid (2-Abz), 3-aminobenzoic acid (3-Abz), 4-aminobenzoic acid (4-Abz), 4-amino-3-hydroxy-6-methylheptanoic acid (Statine, Sta), aminooxyacetic acid (Aoa), 2-aminotetraline-2-carboxylic acid (ATC), 4-amino-5-cyclohexyl-3-hydroxypentanoic acid (ACHPA), para-aminophenylalanine (4-$NH_2$-Phe), 2-aminopimelic acid (Apm), biphenylalanine (Blp), para-bromophenylalanine (4-Br-Phe), ortho-chlorophenylalanine (2-Cl-Phe), meta-chlorophenylalanine (3-Cl-Phe), para-chlorophenylalanine (4-Cl-Phe), meta-chlorotyrosine (3-Cl-Tyr), para-benzoylphenylalanine (Bpa), tert-butylglycine (TLG), cyclohexylalanine (Cha), cyclohexylglycine (Chg), desmosine (Des), 2,2-diaminopimelic acid (Dpm), 2,3-diaminopropionic acid (Dpr), 2,4-diaminobutyric acid (Dbu), 3,4-dichlorophenylalanine (3,4-$C_{12}$-Phe), 3,4-difluororphenylalanine (3,4-$F_2$-Phe), 3,5-diiodotyrosine (3,5-$I_2$-Tyr), N-ethylglycine (EtGly), N-ethylasparagine (EtAsn), ortho-fluorophenylalanine (2-F-Phe), meta-fluorophenylalanine (3-F-Phe), para-fluorophenylalanine (4-F-Phe), meta-fluorotyrosine (3-F-Tyr), homoserine (Hse), homophenylalanine (Hfe), homotyrosine (Htyr), hydroxylysine (Hyl), allo-hydroxylysine (aHyl), 5-hydroxytryptophan (5-OH-Trp), 3- or 4-hydroxyproline (3- or 4-Hyp), para-iodophenylalanine (4-I-Phe), 3-iodotyrosine (3-I-Tyr), indoline-2-carboxylic acid (Idc), isodesmosine (Ide), allo-isoleucine (a-Ile), isonipecotic acid (Inp), N-methylisoleucine (MeIle), N-methyllysine (MeLys), meta-methyltyrosine (3-Me-Tyr), N-methylvaline (MeVal), 1-naphthylalanine (1-Nal), 2-naphthylalanine (2-Nal), para-nitrophenylalanine (4-$NO_2$-Phe), 3-nitrotyrosine (3-$NO_2$-Tyr), norleucine (Nle), norvaline (Nva), ornithine (Orn), ortho-phosphotyrosine ($H_2PO_3$-Tyr), octahydroindole-2-carboxylic acid (Oic), penicillamine (Pen), pentafluorophenylalanine ($F_5$-Phe), phenylglycine (Phg), pipecolic acid (Pip), propargylglycine (Pra), pyroglutamic acid (PGLU), sarcosine (Sar), tetrahydroisoquinoline-3-carboxylic acid (Tic), thienylalanine, and thiazolidine-4-carboxylic acid (thioproline, Th).

"$C_{max}$" refers to the peak plasma concentration of a drug or compound of the invention after administration.

"$T_{max}$" refers to the time to reach $C_{max}$.

"$AUC_{0-t}$" refers to the area under the curve in a plot of plasma concentration of drug or compound of the invention in blood plasma against time. In certain embodiments of the invention, t is infinity ($\infty$) and $AUC_{0-\infty}$ refers to the total drug exposure over time.

"$T_{1/2}$" refers to the biological half-life of a drug and is the time it takes for a drug or compound of the invention to lose half of its pharmacologic, physiologic, or biologic activity.

ApoE4 and Alzheimer's Disease

The ε4 allele of apolipoprotein E gene is the strongest genetic risk factor for patients with late-onset AD. ApoE4+ subjects with at least one ε4 allele account for 50%-60% of AD cases vs. 25% prevalence in healthy individuals. ApoE4+AD patients present with decreased age of onset, increased severity and accelerated progression of AD. Subjects with two ε4 alleles account for 10%-14% of AD and exhibit an even more aggressive disease progression. ε4 allele leads to an increased brain Aβ amyloid deposition, increased CSF tau and p-tau, and faster cognitive decline. In addition, demented patients carrying one or two ε4 alleles of ApoE are more likely to have AD, resulting in significantly reduced rate of disease misdiagnosis in clinical studies (2% vs. 42% in non-ApoE4 patients)

Of patients having dementia, the ApoE4 allele strongly correlates with Alzheimer's Disease, and the presence of ApoE4 alleles is therefore used to reduce misdiagnosis in clinical studies. The rate of a false diagnosis of dementia patients having AD is 2% in ApoE4-positive patients. In contrast, 42% of non-ApoE4 dementia patients are reported to be incorrectly diagnosed as having AD.

Methods and Compositions for Treating ApoE4+ patients

Disclosed herein are methods of treating and/or preventing Alzheimer's disease in patients carrying one or two copies of the ApoE4 allele. Compositions for the treatment and prevention are also disclosed. 3-amino-1-propanesulfonic acid (3-APS, Tramiprosate, Alzhemed™) is a promising investigational product candidate for the treatment of Alzheimer's disease that has undergone Phase III clinical trials in North America and Europe (Wright, T. M., Drugs of Today (2006), 42(5): 291-298). This product was developed by Neurochem Inc. (Laval, QC, Canada) and it is believed to act by reducing the blocking amyloid aggregation, deposition and/or load of amyloid in the brain through its binding to soluble Aβ monomers. For increase the therapeutic effectiveness of 3-APS, it would be desirable to increase exposure of parent after oral administration, metabolic stability and/or increase in exposure of 3-APS, and minimize intersubject pharmacokinetic variability. These and other needs are satisfied by prodrug compounds of 3-amino-1-propanesulfonic acid (3-APS), pharmaceutical compositions thereof. Advantageously, treatment of specific sub-populations with these drugs shows remarkable efficacy. Specifically, disclosed herein are methods for treating and/or preventing Alzheimer's disease in patients who are homozygous or heterozygous for the ApoE4 allele.

Compounds

In one embodiment, the administered compounds are of the following Formula I:

(I)

and pharmaceutically acceptable salts, hydrates, and solvates thereof, wherein $AA_1$ and $AA_2$ are amino acids.

In certain embodiments, $AA_1$ and $AA_2$ are independently selected from the group of natural and unnatural amino acids. In further embodiments, $AA_1$ and $AA_2$ are independently selected from the group of natural amino acids.

In particular embodiments, $AA_1$ and $AA_2$ are independently selected from alanine (Ala), cystein (Cys), aspartic acid (Asp), glutamic acid (Glu), phenylalanine (Phe), glycine (Gly), histidine (His), isoleucine (Ile), lysine (Lys), leucine (Leu), methionine (Met), asparagine (Asn), proline (Pro), glutamine (Gln), arginine (Arg), serine (Ser), threonine (Thr), valine (Val), tryptophan (Trp), tyrosine (Tyr), β-alanine (β-ALA), and γ-aminobutyric acid (GABA). In other aspects, either or both of $AA_1$ and $AA_2$ are O-benzylserine (O-BnSer) or O-benzylglutamine (O-BnGln).

In still further embodiments, $AA_1$ and $AA_2$ of Formula I are the following:

| Compound | $AA_1$ | $AA_2$ |
|---|---|---|
| I-1 | Ala | Ala |
| I-2 | Ala | Arg |
| I-3 | Ala | Asn |
| I-4 | Ala | Asp |
| I-5 | Ala | Cys |
| I-6 | Ala | Gln |
| I-7 | Ala | Glu |
| I-8 | Ala | Gly |
| I-9 | Ala | His |
| I-10 | Ala | Ile |
| I-11 | Ala | Leu |
| I-12 | Ala | Lys |
| I-13 | Ala | Met |
| I-14 | Ala | Phe |
| I-15 | Ala | Pro |
| I-16 | Ala | Ser |
| I-17 | Ala | Thr |
| I-18 | Ala | Trp |
| I-19 | Ala | Tyr |
| I-20 | Ala | Val |
| I-21 | Ala | β-ALA |
| I-22 | Ala | GABA |
| I-23 | Arg | Ala |
| I-24 | Arg | Arg |
| I-25 | Arg | Asn |
| I-26 | Arg | Asp |
| I-27 | Arg | Cys |
| I-28 | Arg | Gln |
| I-29 | Arg | Glu |
| I-30 | Arg | Gly |
| I-31 | Arg | His |
| I-32 | Arg | Ile |
| I-33 | Arg | Leu |
| I-34 | Arg | Lys |
| I-35 | Arg | Met |
| I-36 | Arg | Phe |
| I-37 | Arg | Pro |
| I-38 | Arg | Ser |
| I-39 | Arg | Thr |
| I-40 | Arg | Trp |
| I-41 | Arg | Tyr |
| I-42 | Arg | Val |
| I-43 | Arg | β-ALA |
| I-44 | Arg | GABA |
| I-45 | Asn | Ala |
| I-46 | Asn | Arg |
| I-47 | Asn | Asn |
| I-48 | Asn | Asp |
| I-49 | Asn | Cys |
| I-50 | Asn | Gln |
| I-51 | Asn | Glu |
| I-52 | Asn | Gly |
| I-53 | Asn | His |
| I-54 | Asn | Ile |
| I-55 | Asn | Leu |
| I-56 | Asn | Lys |
| I-57 | Asn | Met |
| I-58 | Asn | Phe |
| I-59 | Asn | Pro |
| I-60 | Asn | Ser |
| I-61 | Asn | Thr |
| I-62 | Asn | Trp |
| I-63 | Asn | Tyr |

-continued

| Compound | AA₁ | AA₂ |
|---|---|---|
| I-64 | Asn | Val |
| I-65 | Asn | β-ALA |
| I-66 | Asn | GABA |
| I-67 | Asp | Ala |
| I-68 | Asp | Arg |
| I-69 | Asp | Asn |
| I-70 | Asp | Asp |
| I-71 | Asp | Cys |
| I-72 | Asp | Gln |
| I-73 | Asp | Glu |
| I-74 | Asp | Gly |
| I-75 | Asp | His |
| I-76 | Asp | Ile |
| I-77 | Asp | Leu |
| I-78 | Asp | Lys |
| I-79 | Asp | Met |
| I-80 | Asp | Phe |
| I-81 | Asp | Pro |
| I-82 | Asp | Ser |
| I-83 | Asp | Thr |
| I-84 | Asp | Trp |
| I-85 | Asp | Tyr |
| I-86 | Asp | Val |
| I-87 | Asp | β-ALA |
| I-88 | Asp | GABA |
| I-89 | Cys | Ala |
| I-90 | Cys | Arg |
| I-91 | Cys | Asn |
| I-92 | Cys | Asp |
| I-93 | Cys | Cys |
| I-94 | Cys | Gln |
| I-95 | Cys | Glu |
| I-96 | Cys | Gly |
| I-97 | Cys | His |
| I-98 | Cys | Ile |
| I-99 | Cys | Leu |
| I-100 | Cys | Lys |
| I-101 | Cys | Met |
| I-102 | Cys | Phe |
| I-103 | Cys | Pro |
| I-104 | Cys | Ser |
| I-105 | Cys | Thr |
| I-106 | Cys | Trp |
| I-107 | Cys | Tyr |
| I-108 | Cys | Val |
| I-109 | Cys | β-ALA |
| I-110 | Cys | GABA |
| I-111 | Gln | Ala |
| I-112 | Gln | Arg |
| I-113 | Gln | Asn |
| I-114 | Gln | Asp |
| I-115 | Gln | Cys |
| I-116 | Gln | Gln |
| I-117 | Gln | Glu |
| I-118 | Gln | Gly |
| I-119 | Gln | His |
| I-120 | Gln | Ile |
| I-121 | Gln | Leu |
| I-122 | Gln | Lys |
| I-123 | Gln | Met |
| I-124 | Gln | Phe |
| I-125 | Gln | Pro |
| I-126 | Gln | Ser |
| I-127 | Gln | Thr |
| I-128 | Gln | Trp |
| I-129 | Gln | Tyr |
| I-130 | Gln | Val |
| I-131 | Gln | β-ALA |
| I-132 | Gln | GABA |
| I-133 | Glu | Ala |
| I-134 | Glu | Arg |
| I-135 | Glu | Asn |
| I-136 | Glu | Asp |
| I-137 | Glu | Cys |
| I-138 | Glu | Gln |
| I-139 | Glu | Glu |
| I-140 | Glu | Gly |
| I-141 | Glu | His |
| I-142 | Glu | Ile |
| I-143 | Glu | Leu |
| I-144 | Glu | Lys |
| I-145 | Glu | Met |
| I-146 | Glu | Phe |
| I-147 | Glu | Pro |
| I-148 | Glu | Ser |
| I-149 | Glu | Thr |
| I-150 | Glu | Trp |
| I-151 | Glu | Tyr |
| I-152 | Glu | Val |
| I-153 | Glu | β-ALA |
| I-154 | Glu | GABA |
| I-155 | Gly | Ala |
| I-156 | Gly | Arg |
| I-157 | Gly | Asn |
| I-158 | Gly | Asp |
| I-159 | Gly | Cys |
| I-160 | Gly | Gln |
| I-161 | Gly | Glu |
| I-162 | Gly | Gly |
| I-163 | Gly | His |
| I-164 | Gly | Ile |
| I-165 | Gly | Leu |
| I-166 | Gly | Lys |
| I-167 | Gly | Met |
| I-168 | Gly | Phe |
| I-169 | Gly | Pro |
| I-170 | Gly | Ser |
| I-171 | Gly | Thr |
| I-172 | Gly | Trp |
| I-173 | Gly | Tyr |
| I-174 | Gly | Val |
| I-175 | Gly | β-ALA |
| I-176 | Gly | GABA |
| I-177 | His | Ala |
| I-178 | His | Arg |
| I-179 | His | Asn |
| I-180 | His | Asp |
| I-181 | His | Cys |
| I-182 | His | Gln |
| I-183 | His | Glu |
| I-184 | His | Gly |
| I-185 | His | His |
| I-186 | His | Ile |
| I-187 | His | Leu |
| I-188 | His | Lys |
| I-189 | His | Met |
| I-190 | His | Phe |
| I-191 | His | Pro |
| I-192 | His | Ser |
| I-193 | His | Thr |
| I-194 | His | Trp |
| I-195 | His | Tyr |
| I-196 | His | Val |
| I-197 | His | β-ALA |
| I-198 | His | GABA |
| I-199 | Ile | Ala |
| I-200 | Ile | Arg |
| I-201 | Ile | Asn |
| I-202 | Ile | Asp |
| I-203 | Ile | Cys |
| I-204 | Ile | Gln |
| I-205 | Ile | Glu |
| I-206 | Ile | Gly |
| I-207 | Ile | His |
| I-208 | Ile | Ile |
| I-209 | Ile | Leu |
| I-210 | Ile | Lys |
| I-211 | Ile | Met |
| I-212 | Ile | Phe |
| I-213 | Ile | Pro |
| I-214 | Ile | Ser |
| I-215 | Ile | Thr |
| I-216 | Ile | Trp |
| I-217 | Ile | Tyr |

-continued

| Compound | AA₁ | AA₂ |
|---|---|---|
| I-218 | Ile | Val |
| I-219 | Ile | β-ALA |
| I-220 | Ile | GABA |
| I-221 | Leu | Ala |
| I-222 | Leu | Arg |
| I-223 | Leu | Asn |
| I-224 | Leu | Asp |
| I-225 | Leu | Cys |
| I-226 | Leu | Gln |
| I-227 | Leu | Glu |
| I-228 | Leu | Gly |
| I-229 | Leu | His |
| I-230 | Leu | Ile |
| I-231 | Leu | Leu |
| I-232 | Leu | Lys |
| I-233 | Leu | Met |
| I-234 | Leu | Phe |
| I-235 | Leu | Pro |
| I-236 | Leu | Ser |
| I-237 | Leu | Thr |
| I-238 | Leu | Trp |
| I-239 | Leu | Tyr |
| I-240 | Leu | Val |
| I-241 | Leu | β-ALA |
| I-242 | Leu | GABA |
| I-243 | Lys | Ala |
| I-244 | Lys | Arg |
| I-245 | Lys | Asn |
| I-246 | Lys | Asp |
| I-247 | Lys | Cys |
| I-248 | Lys | Gln |
| I-249 | Lys | Glu |
| I-250 | Lys | Gly |
| I-251 | Lys | His |
| I-252 | Lys | Ile |
| I-253 | Lys | Leu |
| I-254 | Lys | Lys |
| I-255 | Lys | Met |
| I-256 | Lys | Phe |
| I-257 | Lys | Pro |
| I-258 | Lys | Ser |
| I-259 | Lys | Thr |
| I-260 | Lys | Trp |
| I-261 | Lys | Tyr |
| I-262 | Lys | Val |
| I-263 | Lys | β-ALA |
| I-264 | Lys | GABA |
| I-265 | Met | Ala |
| I-266 | Met | Arg |
| I-267 | Met | Asn |
| I-268 | Met | Asp |
| I-269 | Met | Cys |
| I-270 | Met | Gln |
| I-271 | Met | Glu |
| I-272 | Met | Gly |
| I-273 | Met | His |
| I-274 | Met | Ile |
| I-275 | Met | Leu |
| I-276 | Met | Lys |
| I-277 | Met | Met |
| I-278 | Met | Phe |
| I-279 | Met | Pro |
| I-280 | Met | Ser |
| I-281 | Met | Thr |
| I-282 | Met | Trp |
| I-283 | Met | Tyr |
| I-284 | Met | Val |
| I-285 | Met | β-ALA |
| I-286 | Met | GABA |
| I-287 | Phe | Ala |
| I-288 | Phe | Arg |
| I-289 | Phe | Asn |
| I-290 | Phe | Asp |
| I-291 | Phe | Cys |
| I-292 | Phe | Gln |
| I-293 | Phe | Glu |
| I-294 | Phe | Gly |
| I-295 | Phe | His |
| I-296 | Phe | Ile |
| I-297 | Phe | Leu |
| I-298 | Phe | Lys |
| I-299 | Phe | Met |
| I-300 | Phe | Phe |
| I-301 | Phe | Pro |
| I-302 | Phe | Ser |
| I-303 | Phe | Thr |
| I-304 | Phe | Trp |
| I-305 | Phe | Tyr |
| I-306 | Phe | Val |
| I-307 | Phe | β-ALA |
| I-308 | Phe | GABA |
| I-309 | Pro | Ala |
| I-310 | Pro | Arg |
| I-311 | Pro | Asn |
| I-312 | Pro | Asp |
| I-313 | Pro | Cys |
| I-314 | Pro | Gln |
| I-315 | Pro | Glu |
| I-316 | Pro | Gly |
| I-317 | Pro | His |
| I-318 | Pro | Ile |
| I-319 | Pro | Leu |
| I-320 | Pro | Lys |
| I-321 | Pro | Met |
| I-322 | Pro | Phe |
| I-323 | Pro | Pro |
| I-324 | Pro | Ser |
| I-325 | Pro | Thr |
| I-326 | Pro | Trp |
| I-327 | Pro | Tyr |
| I-328 | Pro | Val |
| I-329 | Pro | β-ALA |
| I-330 | Pro | GABA |
| I-331 | Ser | Ala |
| I-332 | Ser | Arg |
| I-333 | Ser | Asn |
| I-334 | Ser | Asp |
| I-335 | Ser | Cys |
| I-336 | Ser | Gln |
| I-337 | Ser | Glu |
| I-338 | Ser | Gly |
| I-339 | Ser | His |
| I-340 | Ser | Ile |
| I-341 | Ser | Leu |
| I-342 | Ser | Lys |
| I-343 | Ser | Met |
| I-344 | Ser | Phe |
| I-345 | Ser | Pro |
| I-346 | Ser | Ser |
| I-347 | Ser | Thr |
| I-348 | Ser | Trp |
| I-349 | Ser | Tyr |
| I-350 | Ser | Val |
| I-351 | Ser | β-ALA |
| I-352 | Ser | GABA |
| I-353 | Thr | Ala |
| I-354 | Thr | Arg |
| I-355 | Thr | Asn |
| I-356 | Thr | Asp |
| I-357 | Thr | Cys |
| I-358 | Thr | Gln |
| I-359 | Thr | Glu |
| I-360 | Thr | Gly |
| I-361 | Thr | His |
| I-362 | Thr | Ile |
| I-363 | Thr | Leu |
| I-364 | Thr | Lys |
| I-365 | Thr | Met |
| I-366 | Thr | Phe |
| I-367 | Thr | Pro |
| I-368 | Thr | Ser |
| I-369 | Thr | Thr |
| I-370 | Thr | Trp |
| I-371 | Thr | Tyr |

| Compound | AA₁ | AA₂ |
|---|---|---|
| I-372 | Thr | Val |
| I-373 | Thr | β-ALA |
| I-374 | Thr | GABA |
| I-375 | Trp | Ala |
| I-376 | Trp | Arg |
| I-377 | Trp | Asn |
| I-378 | Trp | Asp |
| I-379 | Trp | Cys |
| I-380 | Trp | Gln |
| I-381 | Trp | Glu |
| I-382 | Trp | Gly |
| I-383 | Trp | His |
| I-384 | Trp | Ile |
| I-385 | Trp | Leu |
| I-386 | Trp | Lys |
| I-387 | Trp | Met |
| I-388 | Trp | Phe |
| I-389 | Trp | Pro |
| I-390 | Trp | Ser |
| I-391 | Trp | Thr |
| I-392 | Trp | Trp |
| I-393 | Trp | Tyr |
| I-394 | Trp | Val |
| I-395 | Trp | β-ALA |
| I-396 | Trp | GABA |
| I-397 | Tyr | Ala |
| I-398 | Tyr | Arg |
| I-399 | Tyr | Asn |
| I-400 | Tyr | Asp |
| I-401 | Tyr | Cys |
| I-402 | Tyr | Gln |
| I-403 | Tyr | Glu |
| I-404 | Tyr | Gly |
| I-405 | Tyr | His |
| I-406 | Tyr | Ile |
| I-407 | Tyr | Leu |
| I-408 | Tyr | Lys |
| I-409 | Tyr | Met |
| I-410 | Tyr | Phe |
| I-411 | Tyr | Pro |
| I-412 | Tyr | Ser |
| I-413 | Tyr | Thr |
| I-414 | Tyr | Trp |
| I-415 | Tyr | Tyr |
| I-416 | Tyr | Val |
| I-417 | Tyr | β-ALA |
| I-418 | Tyr | GABA |
| I-419 | Val | Ala |
| I-420 | Val | Arg |
| I-421 | Val | Asn |
| I-422 | Val | Asp |
| I-423 | Val | Cys |
| I-424 | Val | Gln |
| I-425 | Val | Glu |
| I-426 | Val | Gly |
| I-427 | Val | His |
| I-428 | Val | Ile |
| I-429 | Val | Leu |
| I-430 | Val | Lys |
| I-431 | Val | Met |
| I-432 | Val | Phe |
| I-433 | Val | Pro |
| I-434 | Val | Ser |
| I-435 | Val | Thr |
| I-436 | Val | Trp |
| I-437 | Val | Tyr |
| I-438 | Val | Val |
| I-439 | Val | β-ALA |
| I-440 | Val | GABA |
| I-441 | β-ALA | Ala |
| I-442 | β-ALA | Arg |
| I-443 | β-ALA | Asn |
| I-444 | β-ALA | Asp |
| I-445 | β-ALA | Cys |
| I-446 | β-ALA | Gln |
| I-447 | β-ALA | Glu |
| I-448 | β-ALA | Gly |
| I-449 | β-ALA | His |
| I-450 | β-ALA | Ile |
| I-451 | β-ALA | Leu |
| I-452 | β-ALA | Lys |
| I-453 | β-ALA | Met |
| I-454 | β-ALA | Phe |
| I-455 | β-ALA | Pro |
| I-456 | β-ALA | Ser |
| I-457 | β-ALA | Thr |
| I-458 | β-ALA | Trp |
| I-459 | β-ALA | Tyr |
| I-460 | β-ALA | Val |
| I-461 | GABA | β-ALA |
| I-462 | GABA | GABA |
| I-463 | GABA | Ala |
| I-464 | GABA | Arg |
| I-465 | GABA | Asn |
| I-466 | GABA | Asp |
| I-467 | GABA | Cys |
| I-468 | GABA | Gln |
| I-469 | GABA | Glu |
| I-470 | GABA | Gly |
| I-471 | GABA | His |
| I-472 | GABA | Ile |
| I-473 | GABA | Leu |
| I-474 | GABA | Lys |
| I-475 | GABA | Met |
| I-476 | GABA | Phe |
| I-477 | GABA | Pro |
| I-478 | GABA | Ser |
| I-479 | GABA | Thr |
| I-480 | GABA | Trp |
| I-481 | GABA | Tyr |
| I-482 | GABA | Val |
| I-483 | GABA | β-ALA |
| I-484 | GABA | GABA |

Preferred embodiments are: I-11, I-199, I-208, I-214, I-221, I-231, I-236, I-240, I-419, and I-438. Also, preferred are OBnSer-Val, Ile-OBnSer, and OBnSer-Ile.

In an embodiment, disclosed herein are compounds of the following Formula II:

(II)

and pharmaceutically acceptable salts, hydrates, and solvates thereof, wherein AA₁ is an amino acid. In certain embodiments, AA₁ is selected from the group of natural and unnatural amino acids. In further embodiments, AA₁ is selected from the group of natural amino acids.

In particular embodiments, AA₁ is selected from alanine (Ala), cysteine (Cys), aspartic acid (Asp), glutamic acid (Glu), phenylalanine (Phe), glycine (Gly), histidine (His), isoleucine (Ile), lysine (Lys), leucine (Leu), methionine (Met), asparagine (Asn), proline (Pro), glutamine (Gln), arginine (Arg), serine (Ser), threonine (Thr), valine (Val), tryptophan (Trp), tyrosine (Tyr), β-alanine (β-ALA), and γ-aminobutyric acid (GABA). In other aspects, AA₁ is O-benzylserine (O-BnSer) or O-benzylglutamic acid (O-BnGlu).

Thus embodiments disclosed herein include AA₁ of Formula II of the following:

| Compound | AA$_1$ |
| --- | --- |
| II-1 | Ala |
| II-2 | Arg |
| II-3 | Asn |
| II-4 | Asp |
| II-5 | Cys |
| II-6 | Gln |
| II-7 | Glu |
| II-8 | Gly |
| II-9 | His |
| II-10 | Ile |
| II-11 | Leu |
| II-12 | Lys |
| II-13 | Met |
| II-14 | Phe |
| II-15 | Pro |
| II-16 | Ser |
| II-17 | Thr |
| II-18 | Trp |
| II-19 | Tyr |
| II-20 | Val |
| II-21 | β-ALA |
| II-22 | GABA |
| II-23 | O-BnSer |
| II-24 | O-BnGlu |

In particular embodiments, AA1 is selected from Val, Leu, Ser, Ala, OBnSer, and Ile.

Pharmaceutical Compositions

For the purposes of administration, in certain embodiments, the compounds described herein are administered as a raw chemical or are formulated as pharmaceutical compositions. Pharmaceutical compositions of the present disclosure comprise a compound of Formulae I & II and one or more pharmaceutically acceptable carriers. The compound of Formulae I & II is present in the composition in an amount which is effective to treat a particular disease or condition of interest. The activity of compounds of Formulae I & II can be determined by one skilled in the art, for example, as described in the Examples below. Appropriate concentrations and dosages can be readily determined by one skilled in the art.

The compounds and compositions thereof can be administered orally. The compounds and compositions thereof can also be administered by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer a compound. In certain embodiments, more than one compound is administered to a subject. Methods of administration include but are not limited to intradermal, intramuscular (including depot), intraperitoneal, intravenous, subcutaneous (including depot), intranasal, epidural, oral, sublingual (including rapid dissolving tablet, gum or equivalent), intranasal, intracerebral, intravaginal, transdermal, rectally, Intrapulmonary (aerosol or equivalent, including by inhalation), or topically, particularly to the ears, nose, eyes, or skin.

The present compositions comprise a therapeutically effective amount of a compound of the disclosure, optionally more than one compound, together with a suitable amount of a pharmaceutically acceptable vehicle so as to provide a form for administration to the subject.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in "Remington's Pharmaceutical Sciences" by E. W. Martin, incorporated by reference in its entirety for teachings of pharmaceutical compositions and methods of administering the same.

In certain embodiments of the invention a compound of the invention or pharmaceutical salt thereof may be coated on to a medical device suitable for implantation or impregnated into such a medical device. In further embodiments of the invention, such a coated or impregnated device would provide for the controlled release of said compound of the invention or pharmaceutical salt thereof. In particular embodiments of the invention, the medical device is a disc.

In some embodiments, the compounds and compositions are formulated in accordance with routine procedures as a pharmaceutical composition adapted for intravenous administration to humans. Compounds and compositions of the compounds for intravenous administration can be solutions in sterile isotonic aqueous buffer. The compositions can also include a solubilizing agent. The ingredients can be supplied either separately or mixed together in unit dosage form, for example, as a dry lyophilized powder or water free concentrate in a hermetically sealed container such as an ampoule or sachette.

Compounds and compositions of the compounds for oral delivery can be in the form of tablets, lozenges, aqueous or oily suspensions, granules, powders, emulsions, capsules, syrups, or elixirs. Compounds and compositions of the compounds for oral delivery can also be formulated in foods and food mixes. Orally administered compositions can comprise one or more optional agents, for example, sweetening agents such as fructose, aspartame or saccharin; flavoring agents such as peppermint, oil of wintergreen, or cherry; coloring agents; and preserving agents, to provide a pharmaceutically-palatable preparation. The compositions can be coated to delay disintegration and absorption in the gastrointestinal tract thereby providing a sustained action over an extended period of time. Selectively permeable membranes surrounding an osmotically active driving compound are also suitable for orally administered compounds and compositions of the compounds. A time delay material such as glycerol monostearate or glycerol stearate can also be used. Oral compositions can include standard vehicles such as mannitol, lactose, starch, magnesium stearate, sodium saccharine, cellulose, and magnesium carbonate.

In certain embodiments, the compounds or compositions may be in the form of beads or minitabs. Minitabs, also described in the literature as microtabs or minitablets, are small tablets typically having a diameter (or length) of about 0.5 mm to about 10 mm. Minitabs are generally prepared by techniques known in the art, such as wet or dry granulation followed by compression of the granules; direct compression of blended materials, or any other tableting techniques known in the art.

In further embodiments, compounds and compositions of the compounds may be formulated in multi-dose forms, i.e., in the form of multi-particulate dosage forms (e.g., hard gelatin capsules or conventional tablets prepared using a rotary tablet press) comprising one or more bead or minitab populations for oral administration. The conventional tablets rapidly disperse on entry into the stomach. The one or more coated bead or minitab populations may be compressed together with appropriate excipients into tablets (for example, a binder, a diluent/filler, and a disintegrant for conventional tablets.

The tablets, pills, beads, or minitabs of the compounds and compositions of the compounds may be coated or otherwise compounded to provide a dosage form affording the advantage of controlled release, including delayed or extended release, or to protect from the acid conditions of the stomach. For example, the tablet or pill can include an inner dosage and an outer dosage component, the latter being in the form of a coating over the former. The two components can be separated by a polymer layer that controls the release of the inner dosage.

In certain embodiments, the layer may comprise at least one enteric polymer. In further embodiments, the layer may comprise at least one enteric polymer in combination with at least one water-insoluble polymer. In still further embodiments, the layer may comprise at least one enteric polymer in combination with at least one water-soluble polymer. In yet further embodiments, the layer may comprise at least one enteric polymer in combination with a pore-former.

In certain embodiments, the layer may comprise at least one water-insoluble polymer. In still further embodiments, the layer may comprise at least one water-insoluble polymer in combination with at least one water-soluble polymer. In yet further embodiments, the layer may comprise at least one water-insoluble polymer in combination with a pore-former.

Representative examples of water-soluble polymers include polyvinylpyrrolidone (PVP), hydroxypropyl methylcellulose (HPMC), hydroxypropylcellulose (HPC), polyethylene glycol, and the like.

Representative examples of enteric polymers include esters of cellulose and its derivatives (cellulose acetate phthalate, hydroxypropyl methylcellulose phthalate, hydroxypropyl methylcellulose acetate succinate), polyvinyl acetate phthalate, pH-sensitive methacrylic acid-methylmethacrylate copolymers and shellac. These polymers may be used as a dry powder or an aqueous dispersion. Some commercially available materials that may be used are methacrylic acid copolymers sold under the trademark Eudragit (L100, S100, L30D) manufactured by Rohm Pharma, Cellacefate (cellulose acetate phthalate) from Eastman Chemical Co., Aquateric (cellulose acetate phthalate aqueous dispersion) from FMC Corp. and Aqoat (hydroxypropyl methylcellulose acetate succinate aqueous dispersion) from Shin Etsu K.K.

Representative examples of useful water-insoluble polymers include ethylcellulose, polyvinyl acetate (for example, Kollicoat SR#30D from BASF), cellulose acetate, cellulose acetate butyrate, neutral copolymers based on ethyl acrylate and methylmethacrylate, copolymers of acrylic and methacrylic acid esters with quaternary ammonium groups such as Eudragit NE, RS and RS30D, RL or RL30D and the like.

Any of the above polymers may be further plasticized with one or more pharmaceutically acceptable plasticizers. Representative examples of plasticizers include triacetin, tributyl citrate, triethyl citrate, acetyl tri-n-butyl citrate diethyl phthalate, castor oil, dibutyl sebacate, acetylated monoglycerides and the like or mixtures thereof. The plasticizer, when used, may comprise about 3 to 30 wt. % and more typically about 10 to 25 wt. % based on the polymer. The type of plasticizer and its content depends on the polymer or polymers and nature of the coating system (e.g., aqueous or solvent based, solution or dispersion based and the total solids).

The term "carrier" refers to diluents or fillers, disintegrants, precipitation inhibitors, surfactants, glidants, binders, lubricants, anti-oxidants, and other excipients and vehicles with which the compound is administered. Carriers are generally described herein and also in "Remington's Pharmaceutical Sciences" by E. W. Martin. Examples of carriers include, but are not limited to, aluminum monostearate, aluminum stearate, carboxymethylcellulose, carboxymethylcellulose sodium, crospovidone, glyceryl isostearate, glyceryl monostearate, hydroxyethyl cellulose, hydroxyethyl cellulose, hydroxymethyl cellulose, hydroxyoctacosanyl hydroxystearate, hydroxypropyl cellulose, hydroxypropyl cellulose, hydroxypropyl methylcellulose, lactose, lactose monohydrate, magnesium stearate, mannitol, microcrystalline cellulose, poloxamer 124, poloxamer 181, poloxamer 182, poloxamer 188, poloxamer 237, poloxamer 407, povidone, silicon dioxide, colloidal silicon dioxide, silicone, silicone adhesive 4102, and silicone emulsion. It should be understood, however, that the carriers selected for the pharmaceutical compositions provided in the present disclosure, and the amounts of such carriers in the composition, may vary depending on the method of formulation (e.g., dry granulation formulation, solid dispersion formulation).

The term "diluent" or "filler" generally refers to a substance that is used to dilute the compound of interest prior to delivery. Diluents can also serve to stabilize compounds. Examples of diluents may include starch, saccharides, disaccharides, sucrose, lactose, polysaccharides, cellulose, cellulose ethers, hydroxypropyl cellulose, sugar alcohols, xylitol, sorbitol, maltitol, microcrystalline cellulose, calcium or sodium carbonate, lactose, lactose monohydrate, dicalcium phosphate, cellulose, compressible sugars, dibasic calcium phosphate dehydrate, mannitol, microcrystalline cellulose, and tribasic calcium phosphate.

The term "disintegrant" generally refers to a substance which, upon addition to a solid preparation, facilitates its break-up or disintegration after administration and permits the release of an active ingredient as efficiently as possible to allow for its rapid dissolution. Examples of disintegrants may include maize starch, sodium starch glycolate, croscarmellose sodium, crospovidone, microcrystalline cellulose, modified corn starch, sodium carboxymethyl starch, povidone, pregelatinized starch, and alginic acid.

The term "precipitation inhibitors" generally refers to a substance that prevents or inhibits precipitation of the active agent. One example of a precipitation inhibitor includes hydroxypropylmethylcellulose.

The term "surfactants" generally refers to compounds that lower the surface tension between two liquids or between a liquid and a solid. Examples of surfactants include poloxamer and sodium lauryl sulfate.

The term "glidant" generally refers to substances used in tablet and capsule formulations to improve flow-properties during tablet compression and to produce an anti-caking effect. Examples of glidants may include colloidal silicon dioxide, talc, fumed silica, starch, starch derivatives, and bentonite.

The term "binder" generally refers to any pharmaceutically acceptable film which can be used to bind together the active and inert components of the carrier together to maintain cohesive and discrete portions. Examples of binders may include hydroxypropylcellulose, hydroxypropylmethylcellulose, povidone, copovidone, ethyl cellulose, gelatin, and polyethylene glycol.

The term "lubricant" generally refers to a substance that is added to a powder blend to prevent the compacted powder mass from sticking to the equipment during the tableting or encapsulation process. A lubricant can aid the ejection of the tablet form the dies, and can improve powder flow. Examples of lubricants may include magnesium stearate, stearic acid, silica, fats, calcium stearate, polyethylene glycol, sodium stearyl fumarate, or talc; and solubilizers such as fatty acids including lauric acid, oleic acid, and $C_8/C_{10}$ fatty acid.

In certain embodiments, dosage is given with respect to the weight of 3-amino-1-propanesulfonic acid (3-APS or APS). In further embodiments, the dosage refers to the prodrug or compounds of the present disclosure and pharmaceutically acceptable salts, hydrates, and solvates thereof. The dosage amounts described herein refer to total amounts administered; that is, if more than one compound is administered, the dosages can correspond to the total amount of the compounds administered. Oral compositions can comprise 10% to 95% active ingredient by mass.

In certain embodiments, the dosage range for oral administration is generally about 0.001 mg to about 2000 mg of a compound per kg body mass. In some embodiments, the oral dose is 0.01 mg to 100 mg per kg body mass, 0.1 mg to 50 mg per kg body mass, 0.5 mg to 20 mg per kg body mass, or 1 mg to 10 mg per kg body mass. In some embodiments, the oral dose is 5 mg of a compound per kg body mass.

In further embodiments, the dose is about 10 mg to about 1000 mg, including all ranges and subranges there between, e.g., about 10 mg to about 900 mg, about 10 mg to about 800 mg, about 10 to about 700 mg, about 10 mg to about 600 mg, about 10 mg to about 500 mg, about 10 mg to about 400 mg, about 10 mg to about 300 mg, about 10 mg to about 250 mg, about 10 mg to about 200 mg, about 10 mg to about 150 mg, about 10 mg to about 100 mg, about 10 mg to about 50 mg, about 50 mg to about 900 mg, about 50 mg to about 800 mg, about 50 to about 700 mg, about 50 mg to about 600 mg, about 50 mg to about 500 mg, about 50 mg to about 400 mg, about 50 mg to about 300 mg, about 50 mg to about 250 mg, about 50 mg to about 200 mg, about 50 mg to about 150 mg, about 50 mg to about 100 mg, about 100 mg to about 900 mg, about 100 mg to about 800 mg, about 100 to about 700 mg, about 100 mg to about 600 mg, about 100 mg to about 500 mg, about 100 mg to about 400 mg, about 100 mg to about 300 mg, about 100 mg to about 250 mg, about 100 mg to about 200 mg, about 100 mg to about 150 mg, about 150 mg to about 200 mg, about 150 mg to about 250 mg, about 150 mg to about 300 mg, about 150 mg to about 400 mg, about 150 mg to about 500 mg, about 200 mg to about 900 mg, about 200 mg to about 800 mg, about 200 mg to about 700 mg, about 200 mg to about 500 mg, about 200 mg to about 400 mg, about 200 mg to about 300 mg, about 200 mg to about 250 mg, about 300 mg to about 900 mg, about 300 mg to about 800 mg, about 300 to about 700 mg, about 300 to about 600 mg, about 300 mg to about 500 mg, about 300 mg to about 400 mg, about 400 mg to about 900 mg, about 400 mg to about 800 mg, about 400 to about 700 mg, about 400 mg to about 600 mg, about 400 mg to about 500 mg, about 500 mg to about 900 mg, about 500 mg to about 800 mg, about 500 to about 700 mg, about 500 to about 600 mg, about 100 mg to about 500 mg, about 100 mg to about 400 mg, about 100 mg to about 300 mg, about 100 mg to about 250 mg. In particular embodiments, the range is about 150 mg to about 400 mg.

In still further embodiments, the dose is 10 mg, 25 mg, 50 mg, 60 mg, 70 mg, 75 mg, 80 mg, 85 mg, 90 mg, 100 mg, 105 mg, 110 mg, 115 mg, 120 mg, 125 mg, 130 mg, 135 mg, 140 mg, 145 mg, 150 mg, 160 mg, 170 mg, 180 mg, 190 mg, 200 mg, 225 mg, 250 mg, 275 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg.

Methods of Treatment

The disclosure also provides the use of compounds disclosed herein for the manufacture of a medicament in the treatment of ApoE4-postive Alzheimer's patients. The disclosure also provides methods for the treatment or prevention of the aforementioned diseases comprising administration of a therapeutically effective amount of a compound or a composition comprising the same, to a subject, preferably a human subject, in need thereof. Accordingly, a related aspect of the disclosure relates to the prevention and/or treatment of Alzheimer's disease in ApoE4-positive humans by administering an effective amount of a compound or composition of the present disclosure to a human subject in need thereof.

The disclosure also provides for methods for the treatment or prevention of the aforementioned disease comprising administration of a therapeutically effective amount of a compound or a composition comprising the same, to a subject, preferably a human subject, in need thereof where the patient is heterozygous or homozygous for the ApoE4 (or ε4) allele (i.e. ApoE4-postive patients).

Identifying ApoE4-postive patients may be performed by any particular approach capable of determining that a patient as one or two copies of the ApoE4 (or ε4) allele. In particular aspects, sequencing technology is used to genotype the patient prior to administration of a compound.

In certain embodiments, the efficacy of a compound may be determined through the ADAS-cog (Alzheimer's Disease Assessment Scale-cognitive subscale). ADAS was designed to measure the severity of the most important symptoms of Alzheimer's disease (AD). Its subscale ADAS-cog is the most popular cognitive testing instrument used in clinical trials of nootropics. It consists of 11 tasks measuring the disturbances of memory, language, praxis, attention and other cognitive abilities which are often referred to as the core symptoms of AD. The ADAS-Cog helps evaluate cognition and differentiates between normal cognitive functioning and impaired cognitive functioning. It is especially useful for determining the extent of cognitive decline and can help evaluate which stage of Alzheimer's disease a person is in, based on his answers and score. The ADAS-Cog can be used in clinical trials in order to determine incremental improvements or declines in cognitive functioning. An increased ADAS-Cog score compared to placebo demonstrates improved cognitive functioning.

The compounds or a composition comprising a compound may be administered once, twice, three, or four times daily, using any suitable mode described above. Also, in certain embodiments, administration or treatment with the compounds according to any of the formulae described herein may be continued for a number of weeks; for example, commonly treatment would continue for at least 2 weeks, 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 56 weeks, 60 weeks, 64 weeks, 68 weeks, 72 weeks, 76 weeks, 80 weeks, 84 weeks, 88 weeks, 92 weeks, 96 weeks, 100 weeks, or 104 weeks. In yet further embodiments, administration or treatment with the compounds according to any of the formulae described herein may be continued for a number of months; for example, commonly treatment would continue for at least 2 months, 4 months, 6 months, 8 months, 10 months, 12 months, 15 months, 18 months, 20 months, or 24 months. In still further embodiments, administration or treatment with the compounds according to any of the formulae described herein may be continued indefinitely. In still further embodiments, administration or treatment with the compounds according to any of the formulae described herein may be continued until the ADAS-Cog score improves by about 1.5-fold to about 4.5-fold. In some aspects, the improvement in score is about 1.5-fold, about 2.0-fold, about 3.5-fold, about 4.0-fold, about 4.5-fold, about 5.0-fold, about 7.5-fold, about 10.0-fold, about 15.0-fold. In particular aspects, the improvement is about 1.5-fold to about 10.0-fold.

In yet further embodiments, administration or treatment with the compounds according to any of the formulae described herein may be continued until metabolite NRM5074 is present in plasma. Metabolite appearance may be detected and quantified by LC/MS/MS bioanalysis methods.

In a particular embodiment, Val-APS is administered orally in a loose-filled capsule and provides for an extended half-life. For example, the Val-APS supplied in the loose-filled capsule provides a half-life of about 10 h to about 18 hours.

The contents of each cited application and journal article are incorporated by reference as if set forth fully herein.

EXAMPLES

Example 1

Figure 1:
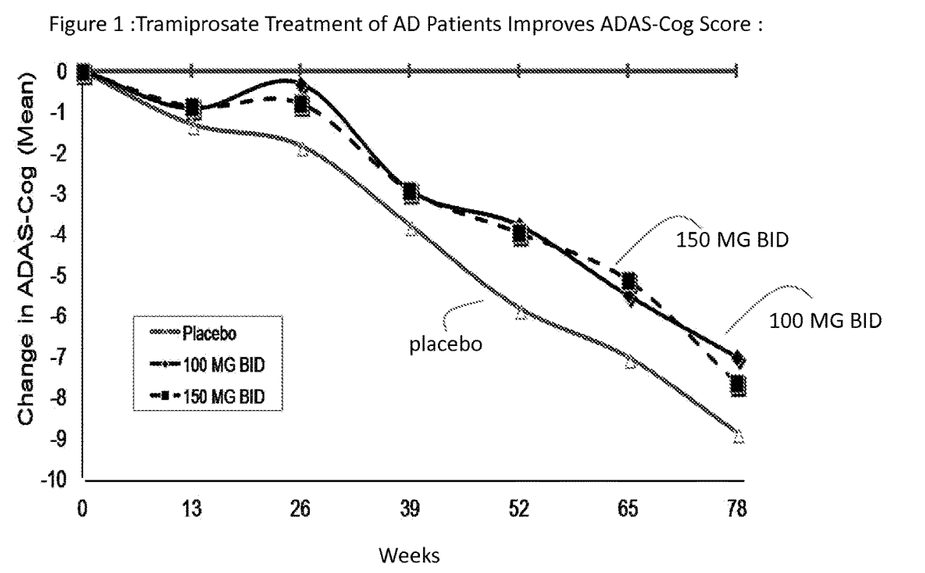
FIG. 1 illustrates reduced ADAS-Cog score following treatment of Alzheimer's Disease patients with tramiprosate. At 26 weeks−1.25 (82%) P=0.0219 for 100 mg BID, −1.03 (57%), P=0.118 for 150 mg BID. At 52 weeks−2.03 (35%) P=0.002 for 100 mg BID, −1.85 (32%), P=0.006 for 150 mg BID. At 65 weeks−1.52 (22%) P=0.024 for 100 mg BID, −1.90 (27%) P=0.005 for 150 mg BID. At 78 weeks−1.90 (27%) P=0.005 for 100 mg BID, −1.86 (21%) P=0.028 for 150 mg BID. (n=599). Data derived from Caltagirone et al., "The potential protective effect of tramiprosate (homotaurine) against Alzheimer's disease: a review," Aging Clin Exp Res. 2012 December; 24(6):580-7.

3APS Treatment Improves ADAS-Cog Scores in ApoE4+ all Comer (Heterozygous and Homozygous) Subjects Patients were administered 3APS at 150 mg BID and 100 mg BID or were provided a placebo. ADAS-Cog results were measured. The data establish that the decline in score is delayed by 3APS. See FIG. 1 and tables below. At 13 weeks a small improvement in ADAS-cog was observed. Over time, the difference increased. From ~52 weeks the placebo patients showed substantially greater declines in cognition compared to both treated arms of the study (i.e. 100 mg BID and 150 mg BID).

ADAS-Cog by ApoE4 Subgroup in Merged Dataset

| Effect | Total | | ApoE4+ | | ApoE4− | |
|---|---|---|---|---|---|---|
| Group n | p 0.10 1691 | | p 0.02 1062 | | p 0.44 629 | |
| | 100 mg BID | 150 mg BID | 100 mg BID | 150 mg BID | 100 mg BID | 150 mg BID |
| n week 13 | 548 | 554 | 342 | 337 | 206 | 217 |
| Slope vs placebo | −3.18 (p 0.13) | −4.19 (p 0.04) | −3.61 (p 0.17) | −7.09 (p 0.0048) | −2.45 (p 0.50) | 0.35 (p 0.92) |
| Week 78 | −1.34 (p 0.0098) | −1.27 (p 0.0121) | −1.09 (p 0.09) | −1.73 (p 0.005) | −1.92 (p 0.03) | −0.66 (p 0.46) |

Change in ADAS-Cog by APOE STATUS (<80 Years Old) in Merged Dataset

| Effect | Total | | ApoE4+ | | ApoE4− | |
|---|---|---|---|---|---|---|
| Group n week 13 | p 0.017 1392 | | p 0.0051 909 | | p 0.57 483 | |
| | 100 mg BID | 150 mg BID | 100 mg BID | 150 mg BID | 100 mg BID | 150 mg BID |
| n week 13 | 459 | 451 | 307 | 282 | 152 | 169 |
| Slope vs placebo | −3.94 (p 0.09) | −6.37 (p 0.0045) | −3.92 (p 0.16) | −8.65 (p 0.001) | −4.40 (p 0.30) | −2.81 (p 0.51) |
| Week 78 | −1.55 (p 0.007) | −1.66 (p 0.003) | −1.13 (p 0.099) | −2.17 (p 0.0009) | −2.54 (p 0.01) | −0.93 (p 0.38) |

Change in ADAS-Cog by ApoE Status in North American Trial

| Effect | Total | | ApoE4+ and ++ | | ApoE4++ | | ApoE4− | |
|---|---|---|---|---|---|---|---|---|
| n for group | 894 | | 562 | | 120 | | 332 | |
| | 100 mg BID | 150 mg BID | 100 mg BID | 150 mg BID | 100 mg BID | 150 mg BID | 100 mg BID | 150 mg BID |
| Slope vs placebo | −1.75 (p 0.44) | −3.32 (p 0.14) | −1.43 (p 0.62) | −7.49 (p 0.009) | −4.33 (p 0.464) | −19.79 (p 0.001) | −2.04 (p 0.59) | 3.57 (p 0.36) |
| Week 78 | −0.93 (p 0.13) | −0.83 (p 0.17) | −0.81 (p 0.30) | −1.67 (p 0.03) | −1.49 (p 0.33) | −4.63 (p 0.004) | −1.23 (p 0.23) | 0.59 (p 0.57) |

Figure 2:
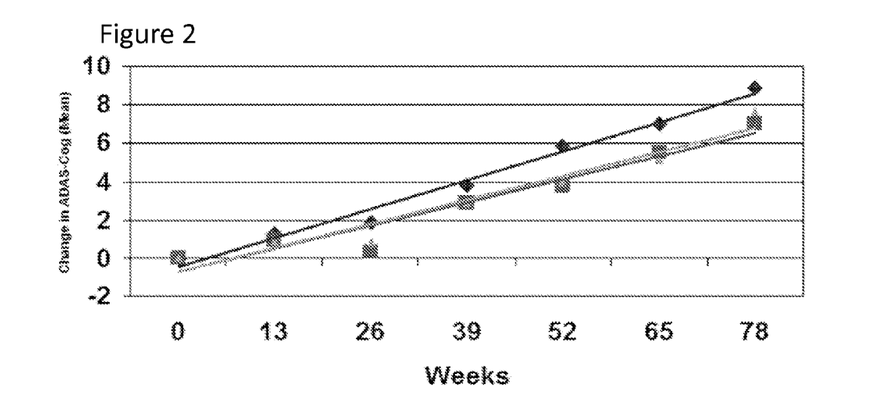
FIGS. 2 and 3: Retrospective subgroup analysis in 599 ApoE4+ subjects using mixed effects repeated measures, covariate model (MERM) demonstrated a significant effect on both cognition and function utilizing ADAS-cog and CDR-SB.
Figure 3:
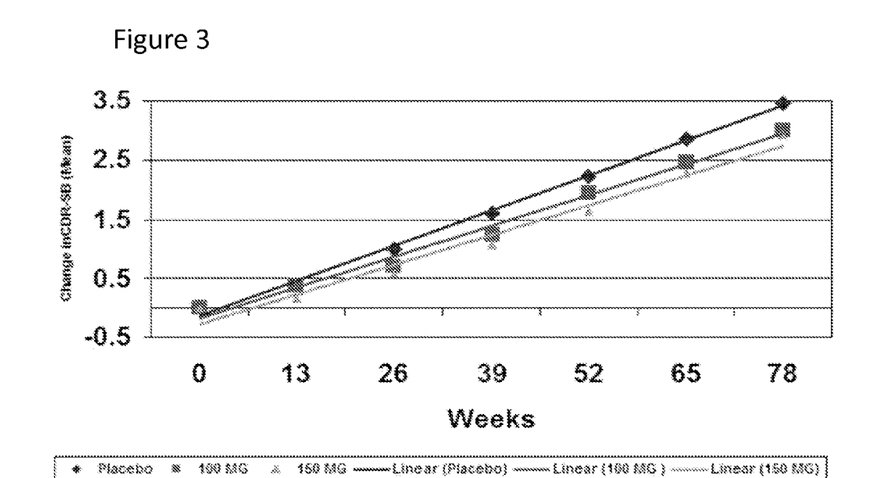

Tramiprosate also produced a clinically meaningful improvement in cognition (ADAS-cog) and function (CDR-SB) through 18 months, on top of treatment with acetylcholinesterase inhibitors and/or memantine (tramiprosate 150 mg BID, n=183; ADAS-cog: slope vs. placebo p<0.01, and p<0.05 at Week 78; CDR-SB: slope vs. placebo p<0.01, and p<0.05 at Week 78). See FIGS. 2 and 3.

Example 2

Figure 4:
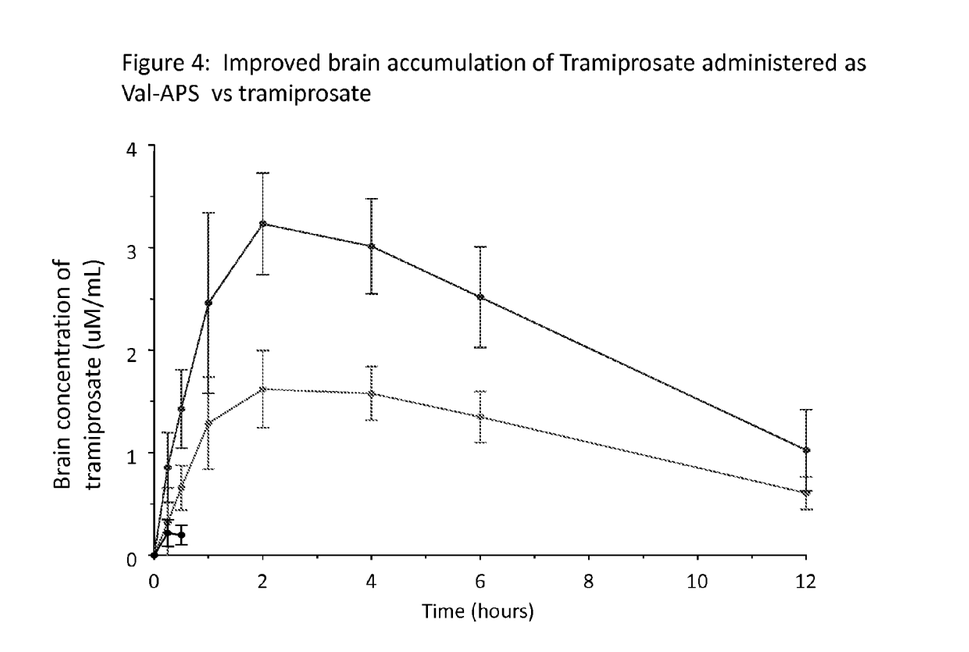
FIG. 4 shows Brain exposure of tramiprosate after oral Val-APS (upper line) or tramiprosate (lower line). The AUC ratio of brain tramiprosate exposure due to Val-APS compared to tramiprosate is ~2.1.
Figure 5:
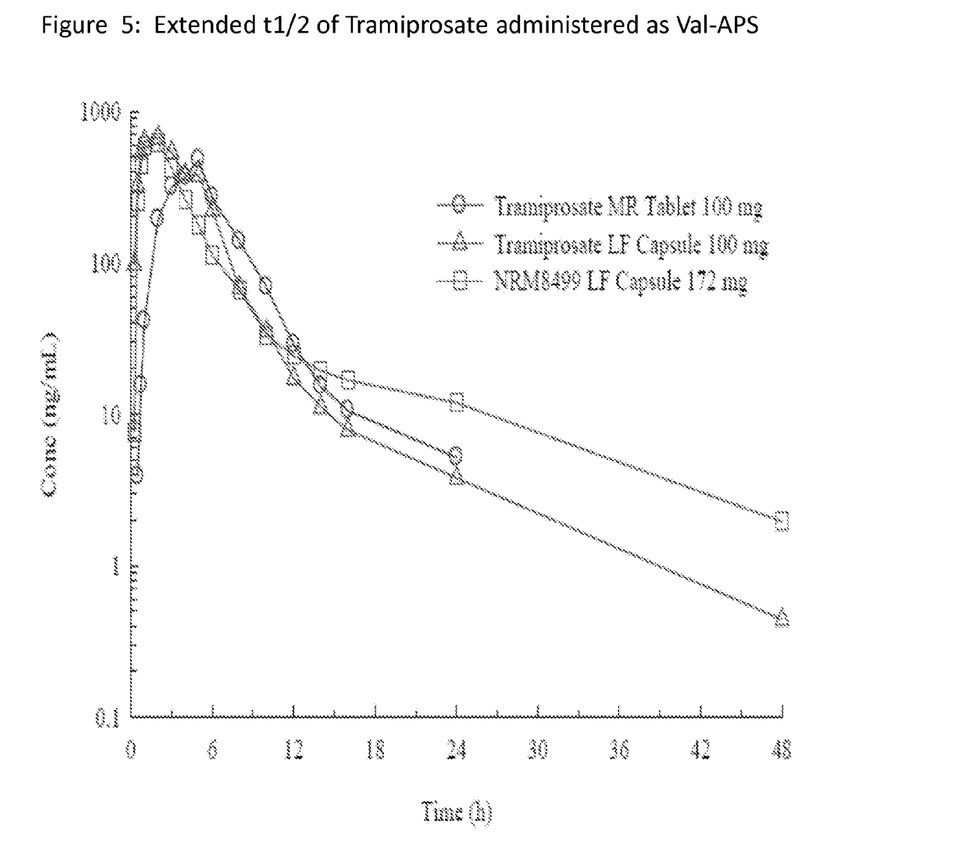
FIG. 5 shows Phase 1 SAD trial results in normal healthy elderly subjects demonstrating that oral Val-APS prodrug provides extended $t_{1/2}$ of tramiprosate.
Figure 6:
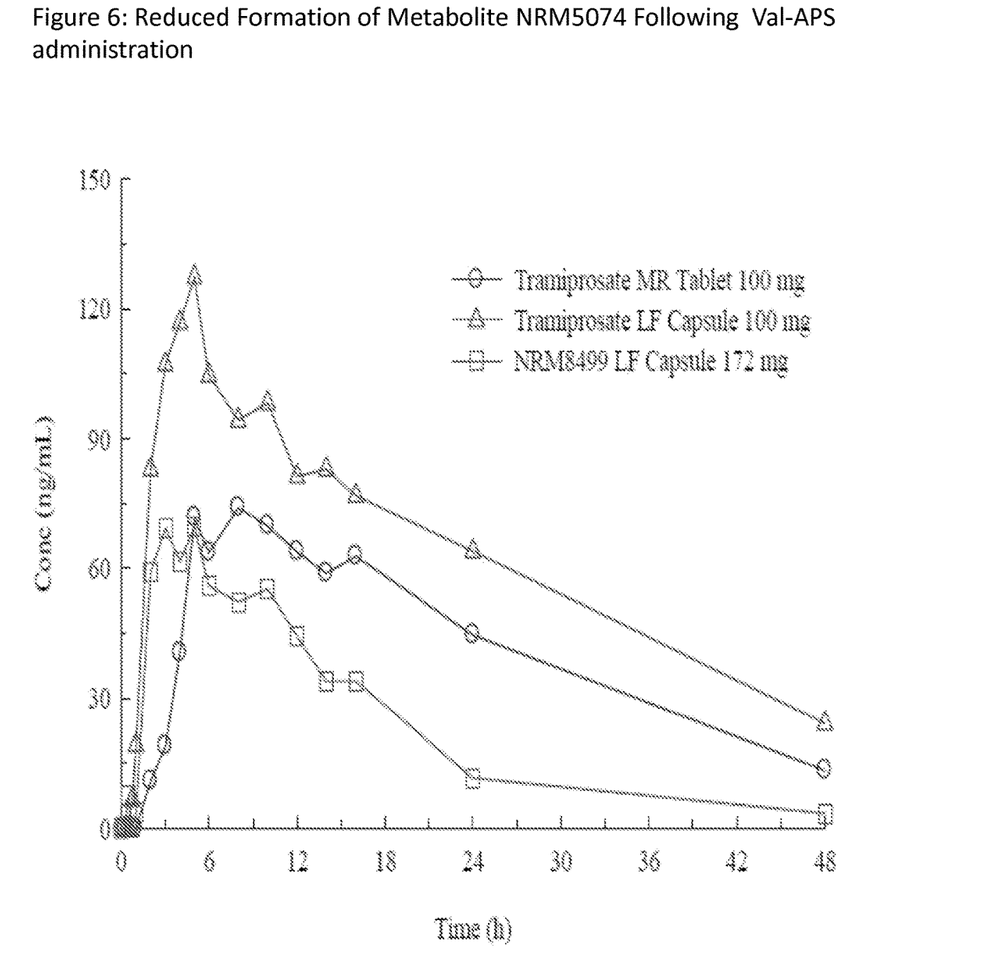
FIG. 6 shows Phase 1 SAD trial results in normal healthy elderly subjects showing reduced formation of metabolite NRM5074 following Val-APS administration
Figure 7:
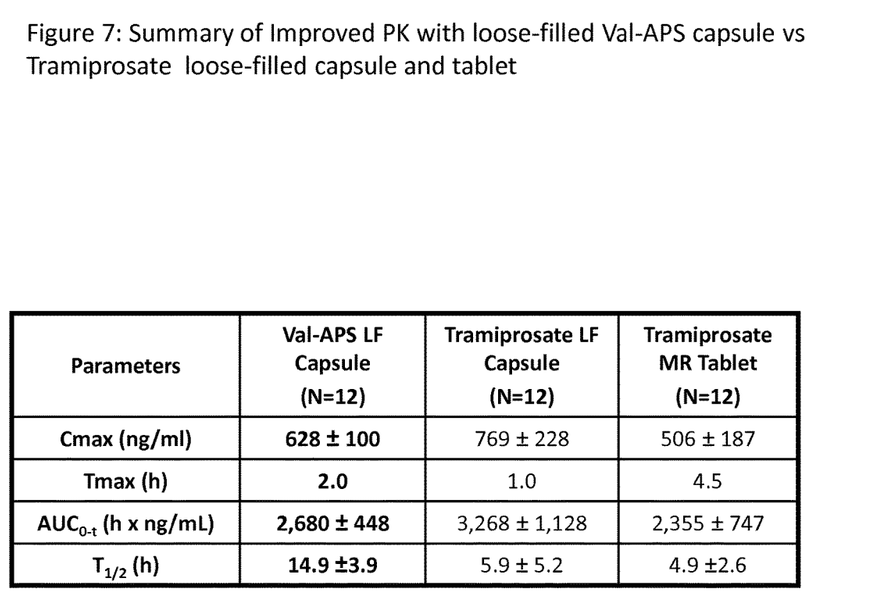
FIG. 7 shows a SAD study in normal HV demonstrating that orally administered Val-APS displays a reduction in PK variability superior to MR tablet or LF capsule tramiprosate. Val-APS loose filled capsule reduces PK variability by ~50% and, furthermore, the terminal $t_{1/2}$ is extended to 14.9 hours, allowing once-daily dosing.

Val-APS Shows Improved Brain Accumulation and Improved Plasma Half-life Relative to 3APS FIG. 4 illustrates the improved accumulation in the brain obtained with the Val-APS prodrug versus tramiprosate. By using the prodrug, enhanced accumulation at the site of action is achieved. FIG. 5 further illustrates the improved pharmacological qualities of Val-APS. When tramiprosate is administered as Val-APS, (NRM8499), the APS exhibits an extended t½. FIG. 7 summarises data showing the improved qualities of the loose-filled Val-APS capsule over 3APS (tramiprosate) in capsule and tablet form. The data shows an increase in t½ to 14.9 ±3.9 when Val-APS is administered in a loose-fill capsule.

Example 3

3APS Exhibits Pronounced Effects in ApoE4-Positive Patients

Figure 8:
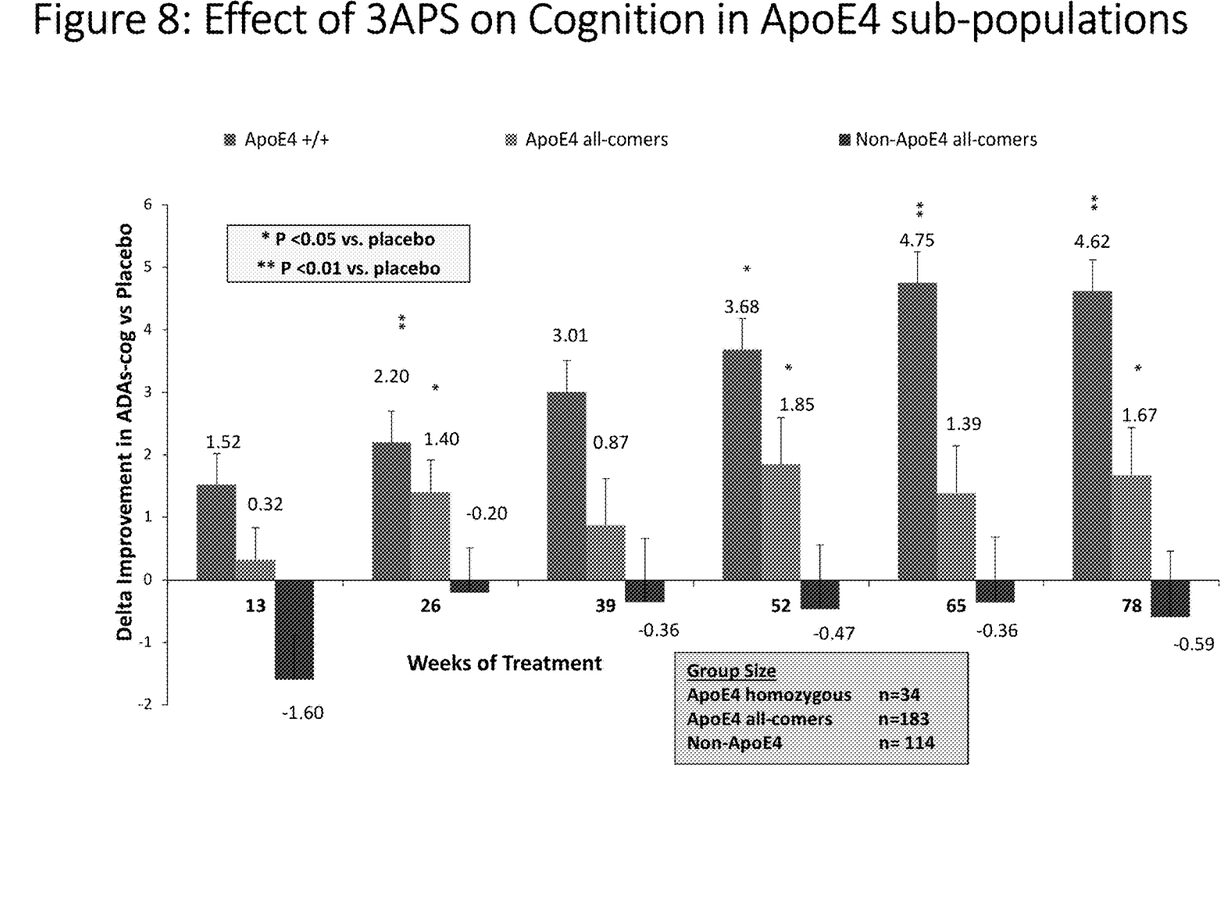

Patients were administered 3APS and ADAS-Cog results were obtained at various timepoints. Patients were then genotyped to detect the presence of ApoE4 alleles. FIG. 8 illustrates the advantageous effects of tramiprosate, the active agent of Val-APS, in certain sub-populations segregated based on Apo E4 status. The data established substantially improved ADAs-cog scores vs placebo over time. Data is presented at 13 weeks, 26 weeks, 39 weeks, 52 weeks, 65 weeks, and 78 weeks. The first column shows patients homozygous for ApoE4 ("ApoE4 +/+"), the second column shows combined data from ApoE4 heterozygous and homozygous patients "ApoE4 all-comers", the third column shows patients negative for ApoE4 (Non-ApoE4). ApoE4 prevalence correlates with improved cognition scores. Notably, patients that were homozygous for the E4 allele showed particularly pronounced improvements. Taken as a whole, these data show a 4 point improvement versus placebo on cognition in homozygous ApoE4 subjects (tramiprosate; 150 mg BID, n=34) reaching 4.62 points on the ADAS-cog after 18 months of treatment (p<0.01).

The invention claimed is:

1. A method of selecting and treating a patient suffering from Alzheimer's disease comprising the steps of:
    (a) selecting the patient as having a tramiprosate-sensitive form of Alzheimer's disease based on the presence of two ApoE4 alleles; and
    (b) administering to the selected patient tramiprosate in an amount effective to treat the disease.

2. The method of claim 1, wherein the administration of the compound to the patient is for a period of greater than 13 weeks.

3. A method of selecting and treating a patient suffering from Alzheimer's disease comprising the steps of:
    (a) selecting the patient as having a tramiprosate-sensitive form of Alzheimer's disease based on the presence of two ApoE4 alleles; and
    (b) administering to the selected patient a compound having the formula:

in an amount effective to treat the disease.

4. The method of claim 1, wherein the treatment reduces cognitive decline in the patient.

5. The method of claim 3, wherein the treatment reduces cognitive decline in the patient.

6. The method of claim 1, wherein the compound is administered in an oral dosage form.

7. The method of claim 6, wherein the dosage range is between about 100 mg to about 150 mg.

8. The method of claim 3, wherein the administration of the compound to the patient is for a period of greater than 13 weeks.

9. The method of claim 3, wherein the compound is administered in an oral dosage form.

10. The method of claim 9, wherein the dosage range is between about 150 mg to about 300 mg.

11. The method of claim 6, wherein the compound is administered twice daily.

12. The method of claim 7, wherein the compound is administered twice daily.

13. The method of claim 9, wherein the compound is administered twice daily.

14. The method of claim 10, wherein the compound is administered twice daily.

* * * * *

UNITED STATES PATENT AND TRADEMARK OFFICE
CERTIFICATE OF CORRECTION

| | |
|---|---|
| PATENT NO. | : 10,471,029 B2 |
| APPLICATION NO. | : 15/127565 |
| DATED | : November 12, 2019 |
| INVENTOR(S) | : Tolar et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 47 days.

Signed and Sealed this
Twentieth Day of December, 2022

*Katherine Kelly Vidal*

Katherine Kelly Vidal
*Director of the United States Patent and Trademark Office*